United States Patent
He et al.

(10) Patent No.: US 10,881,667 B2
(45) Date of Patent: Jan. 5, 2021

(54) METHOD AND COMPOSITION FOR TREATING EPILEPSY

(71) Applicant: City University of Hong Kong, Kowloon (HK)

(72) Inventors: Jufang He, Kowloon (HK); Xiao Li, Kowloon (HK); Ailian Tan, Kowloon (HK); Yujie Peng, Kowloon (HK); Shenghui Xu, Kowloon (HK); Yujie Yang, Kowloon (HK); Xu Zhang, Kowloon (HK); MD. Monir Hossain, Kowloon (HK)

(73) Assignee: City University of Hong Kong, Kowloon (HK)

(*) Notice: Subject to any disclaimer, the term of this patent is extended or adjusted under 35 U.S.C. 154(b) by 0 days.

(21) Appl. No.: 16/174,842

(22) Filed: Oct. 30, 2018

(65) Prior Publication Data

US 2020/0129521 A1  Apr. 30, 2020

(51) Int. Cl.
*A61K 31/5513* (2006.01)
*A61P 25/08* (2006.01)

(52) U.S. Cl.
CPC .......... *A61K 31/5513* (2013.01); *A61P 25/08* (2018.01)

(58) Field of Classification Search
CPC .................. A61K 31/5513; A61P 25/08
See application file for complete search history.

(56) References Cited

U.S. PATENT DOCUMENTS

| | | | |
|---|---|---|---|
| 5,637,585 A | 6/1997 | Nakamura et al. | |
| 5,688,943 A * | 11/1997 | Ryder ................. | C07D 243/24 540/509 |
| 5,728,829 A | 3/1998 | Semple et al. | |
| 2004/0138207 A1 | 7/2004 | Yamano | |
| 2008/0124741 A1 | 5/2008 | Dai et al. | |
| 2018/0215728 A1 | 8/2018 | Boyce et al. | |

FOREIGN PATENT DOCUMENTS

| | | |
|---|---|---|
| EP | 0508799 | 10/1992 |
| GB | 2259013 | 3/1993 |
| WO | 9211246 | 7/1992 |
| WO | 2005007107 | 1/2005 |
| WO | 2015077572 | 5/2015 |

OTHER PUBLICATIONS

Lee et al. Dev. Neurobiol., 2011, vol. 71, No. 1, pp. 83-91. or pp. 1-14.*
G, Zetler, "Anticonvulsant Effects of Caerulein, Cholecystokinin Octapeptide (CCK-8) and Diazepam against Seizures Produced in Mice by Harman, Thiosemicarbazide and Isoniazid". Neuroscience Letters; 24 (1981) 175-180.
Kadar T et al, "Multiple Treatment Potentiates the Anticonvulsive Activity of Cholecystokinin Octapeptides". Peptides; Nov.-Dec. 1985;6(6):1009-14.
Mohammad, A. et al. Ameliorating effects of proglumide on 1, 6-9, 14-neurobehavioral and biochemical deficits in animal model of status epilepticus. Pakistan Journal of Pharmaceutical Sciences. Nov. 30, 2014(Nov. 30, 2014) No. 06 vol. 27 ISSN:I011-601X see pp. 1945-1951, especially see the abstract.
Ni, Hong Anticonvulsant effect of cholecystokinin. Foreign Medical 1-14—Sciences Section on Neurology & Neurosurgery. Feb. 28, 2002(Feb. 28, 2002) No. 01 vol. 29 ISSN: 1673-2642 see pp. 65-67.

* cited by examiner

*Primary Examiner* — Samira J Jean-Louis
(74) *Attorney, Agent, or Firm* — Renner Kenner Greive Bobak Taylor & Weber

(57) ABSTRACT

A method of treating a subject suffering from epilepsy includes administering an effective amount of a cholecystokinin-2 receptor antagonist or a pharmaceutical acceptable salt thereof to the subject. A pharmaceutical composition includes the cholecystokinin-2 receptor antagonist or a pharmaceutical acceptable salt thereof as active ingredient, one or more antiepileptic compounds, and a pharmaceutically acceptable excipient.

7 Claims, 2 Drawing Sheets

METHOD AND COMPOSITION FOR TREATING EPILEPSY

TECHNICAL FIELD

The present invention relates to a method of treating epilepsy in a subject, in particular, but not exclusively, by administering a cholecystokinin (CCK) receptor antagonist to the subject. The invention also relates to a pharmaceutical composition for said method.

BACKGROUND OF THE INVENTION

Epilepsy is a group of neurological disorders characterized by unpredictable occurrence of seizures. Seizures that occur without evident provocation are classified as epileptic. A subject is typically considered as suffering from epilepsy upon experiencing seizures for two or more times. There are about 50 million epilepsy patients in the world, according to Patrick Kwan et al. *New England Journal of Medicine*, 2011, 365(10): 919-926.

Antiepileptic drugs mainly modulate voltage sensitive ion channels, GABA receptor or GABA metabolism. Whilst a large part of patients responds to antiepileptic drug therapy, there is about 20%-30% of epilepsy patients are refractory to the treatments (i.e. resistant to the antiepileptic drug therapy). In general, the refractory epilepsy patients may be administered with a combination of drugs having different pharmacologic mechanism. Accordingly, there still remains a strong need for novel and effective approach in treating epilepsy.

SUMMARY OF THE INVENTION

In this invention, the inventors unexpectedly found that cholecystokinin-2 (CCK2) receptor antagonist are useful in treating epilepsy. In contrast to the known mechanism which activates the CCK receptors as described in *Neuroscience Letter*, 1981, 24(2): 175-180, it was found that the inhibition on CCK2 receptors of the present invention can effectively reduce the occurrence of spontaneous seizures.

In a first aspect, the present invention provides a method of treating a subject suffering from epilepsy comprising the step of administering an effective amount of a CCK2 receptor antagonist to the subject.

The CCK2 receptor antagonist administered according to the present invention has a structure of Formula (Ia) including any pharmaceutical acceptable salt thereof:

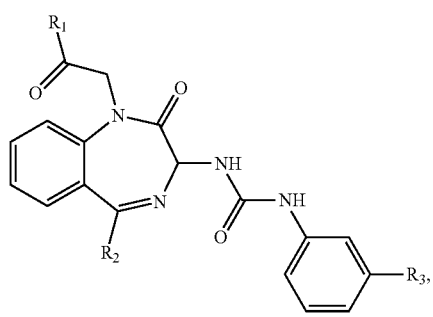

Formula (Ia)

wherein $R_1$ and $R_2$ are independently a hydrogen atom, a substituted or unsubstituted linear or branched chain C1 to C5 alkyl group, a substituted or unsubstituted aryl group, or a heteroaryl; and $R_3$ is a hydrogen atom, a substituted or unsubstituted linear or branched chain C1 to C3 alkyl group, or a C1 to C3 alkylamino group.

In particular, the CCK2 receptor antagonist has a structure of Formula (Ia) with $R_1$ being a linear or branched chain C1 to C4 alkyl group, or a substituted or unsubstituted aryl group; $R_2$ being a substituted or unsubstituted aryl group, or a heteroaryl; and $R_3$ being a methyl group, an ethyl group, a methylamino group or an ethylamino group.

Preferably, the CCK2 receptor antagonist has a structure of Formula (IIa) or Formula (IIIa):

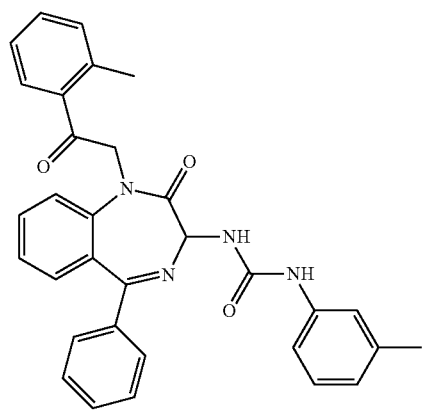

Formula (IIa)

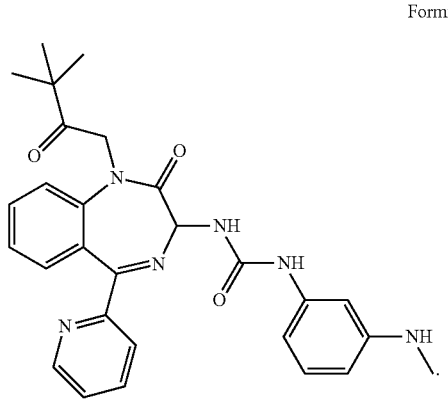

Formula (IIIa)

More preferably, the CCK2 receptor antagonist has a structure of Formula (IIb) or Formula (IIIb):

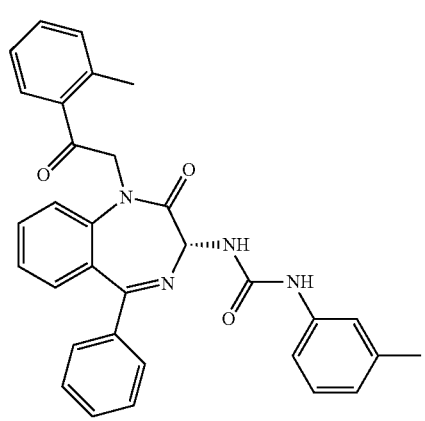

Formula (IIb)

Formula (IIIb)

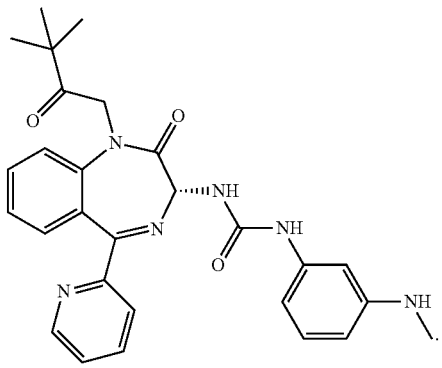

In an embodiment, the CCK2 receptor antagonist is administered in combination with one or more antiepileptic compounds to the subject. In particular, the antiepileptic compounds is selected from the group consisting of primidone, diazepam, perampanel, tiagabine, methsuximide, ethosuximide, stiripentol, phenobarbital sodium, felbamate, acetazolamide, brivaracetam, benzobarbital, phenytoin sodium, clobazam, fosphenytoin sodium, ezogabine, lacosamide, eslicarbazepine, topiramate, oxcarbazepine, zonisamide, lamotrigine, carbamazepine, clonazepam, vigabatrin, levetiracetam, divalproex sodium, valproic acid, lorazepam, clorazepate, and gabapentin.

In an embodiment, the CCK2 receptor antagonist is administered to the subject via injection.

In a second aspect, the present invention pertains to a pharmaceutical composition comprising a CCK2 receptor antagonist as described above, or a pharmaceutical acceptable salt thereof as active ingredient and one or more antiepileptic compounds. Preferably, the antiepileptic compound is selected from the group consisting of primidone, diazepam, perampanel, tiagabine, methsuximide, ethosuximide, stiripentol, phenobarbital sodium, felbamate, acetazolamide, brivaracetam, benzobarbital, phenytoin sodium, clobazam, fosphenytoin sodium, ezogabine, lacosamide, eslicarbazepine, topiramate, oxcarbazepine, zonisamide, lamotrigine, carbamazepine, clonazepam, vigabatrin, levetiracetam, divalproex sodium, valproic acid, lorazepam, clorazepate, and gabapentin.

Particularly, the inventor found that the benzodiazepine compounds, i.e. compound of Formula (IIb) and Formula (IIIb) (each referred as YM022 and YF476 respectively) can selectively inhibit CCK2 receptors. These two compounds are generally applied in the treatment and/or prevention of gastric and duodenal ulceration, gastritis, reflux esophagitis, Zollinger-Ellison syndrome, anxiety, osteoporosis, neuroendocrine tumors and digestive system tumors, but not epilepsy. The experimental results of the present invention indicate that YM022 and YF476 can significantly reduce spontaneous seizures onset for mice suffering from epilepsy. In addition, it is found that these compounds have a long half-life in vivo, providing prolonged seizure inhibiting effects. In particular, a single administration of these compounds is already capable of reducing seizure frequency for at least 3 days whilst administration of the antiepileptic drugs currently used in clinical requires at least once daily to achieve a similar goal. Accordingly, it is believed that these compounds are effective in treating epilepsy, and may be further applied in the development of medicament for treating refractory epilepsy.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1:
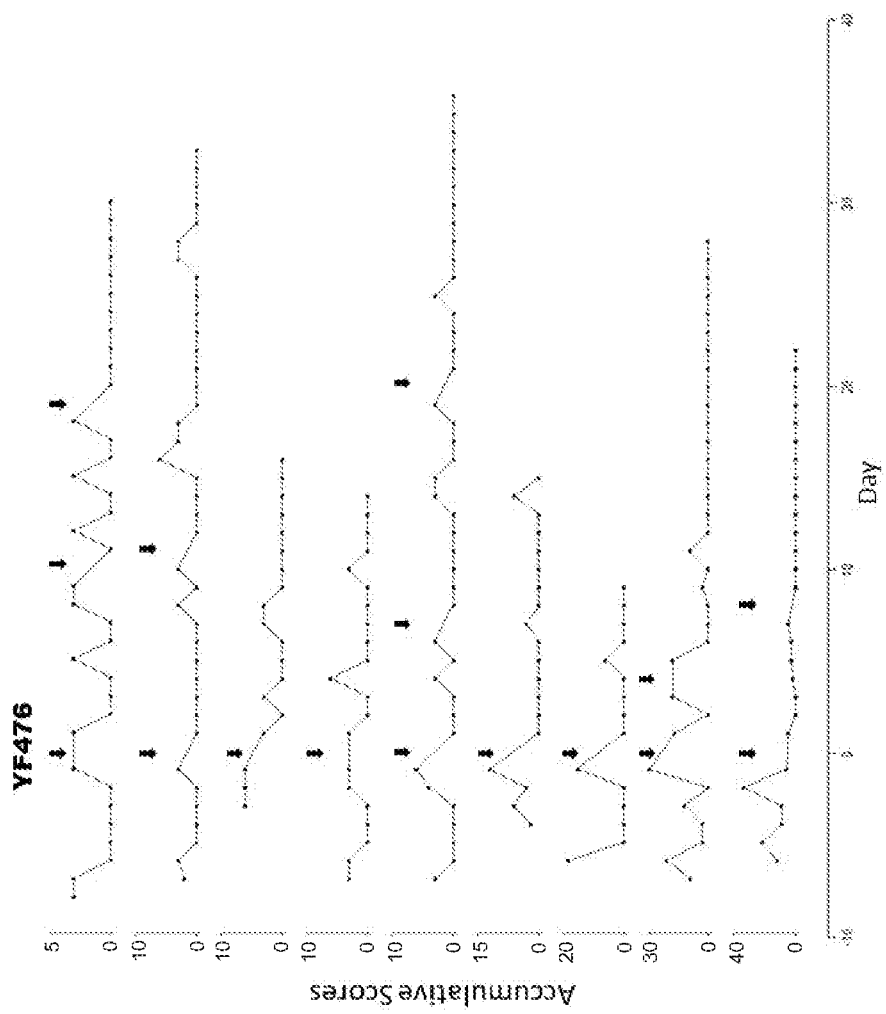
FIG. 1 is a series of line plots depicting the statistics of the accumulative scores of spontaneous seizures of epilepsy model mice before and after single or multiple drug interventions (YM476, 1 µM, 10 µL). The 9 lines represent 9 epilepsy model mice of the experiment, and the black arrows indicate the time of drug interventions. Accumulative scores were recorded base on the quantity and severity of spontaneous seizures: 3=Racine scale stage-5 seizure; 2=Racine scale stage-4 seizure; 1=Racine scale stage-3 seizure; accumulative score is equal to sum of scores of seizures on daily basis.

Unless otherwise defined, all technical terms used herein have the same meaning as commonly understood by one skilled in the art to which the invention belongs.

As used herein, "comprising" means including the following elements but not excluding others. "Consisting of" means that the material solely consists of, i.e. is formed by the respective element. As used herein, the forms "a," "an," and "the", are intended to include the singular and plural forms unless the context clearly indicates otherwise.

The present invention in the first aspect provides a method of treating a subject suffering from epilepsy. The method comprises a step of administering an effective amount of a cholecystokinin-2 (CCK2) receptor antagonist to the subject. The term "CCK receptor antagonist" used herein generally refers to a specific type of receptor antagonist that blocks the receptor sites for the peptide hormone CCK. It is appreciated in the art that there are two subtypes of receptor, namely CCK1 receptor and CCK2 receptor (also known as CCK A receptor and CCK B receptor). The CCK receptor antagonist is defined by its selectivity towards each subtype of receptor, namely CCK1 receptor antagonist and CCK2 receptor antagonist.

The CCK2 receptor antagonist of the present invention may be a modified peptide molecule or a non-peptide molecule.

In an embodiment, the CCK2 receptor antagonist has a structure of Formula (Ia):

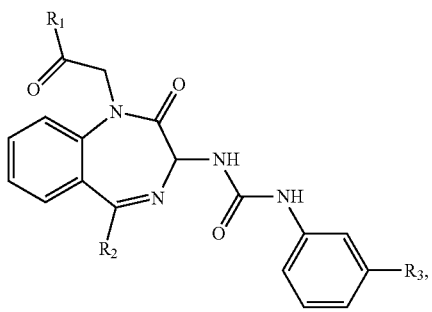

Formula (Ia)

wherein $R_1$ and $R_2$ are independently a hydrogen atom, a substituted or unsubstituted linear or branched chain C1 to C5 alkyl group, a substituted or unsubstituted aryl group, or a heteroaryl; and $R_3$ is a hydrogen atom, a substituted or unsubstituted linear or branched chain C1 to C3 alkyl group, or a C1 to C3 alkylamino group.

The inventors found that the CCK2 receptor antagonist having the Formula (Ia) or preferably Formula (Ib) below is exceptionally suitable for inhibiting the recurrent seizures

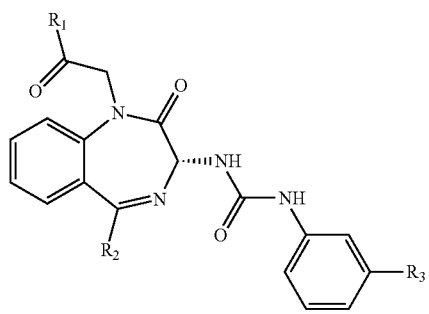

Formula (Ib)

wherein $R_1$, $R_2$ and $R_3$ are as defined above.

In particular, $R_1$ is a linear or branched C1 to C4 alkyl group such as methyl, ethyl, propyl, butyl, isopropyl, tert-butyl, or an unsubstituted aryl group such as phenyl, or a substituted aryl group such as tolyl, xylyl, naphthyl, halophenyl, thiophenyl, or aminophenyl. $R_2$ is the aforementioned substituted or unsubstituted aryl group, or a heteroaryl group such as pyridyl, pyrimidinyl, thienyl, imidazopyridyl, or pyrazolyl. $R_3$ is a methyl, an ethyl, a methylamino, or an ethylamino group.

In a preferred embodiment, the CCK2 receptor antagonist has a structure of Formula (IIa) or Formula (Ia):

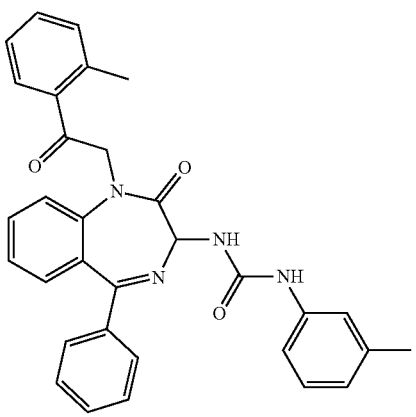

Formula (IIa)

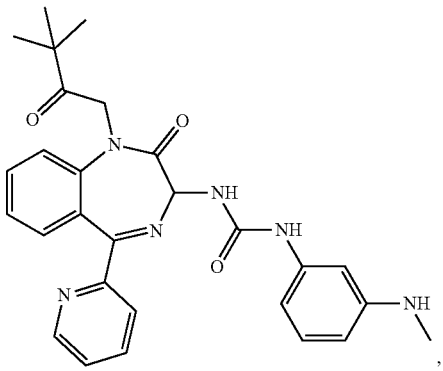

Formula (IIIa)

including any pharmaceutically acceptable, solvate or anhydrate thereof and including any stereoisomer, diastereomer, enantiomer or racemate thereof.

In particular, the CCK2 receptor antagonist has a structure of Formula (IIb) or Formula (IIIb)

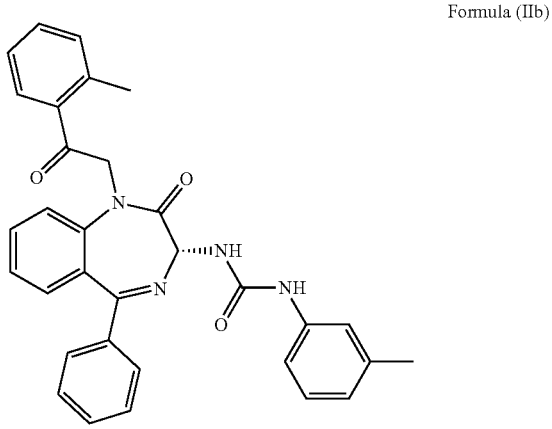

Formula (IIb)

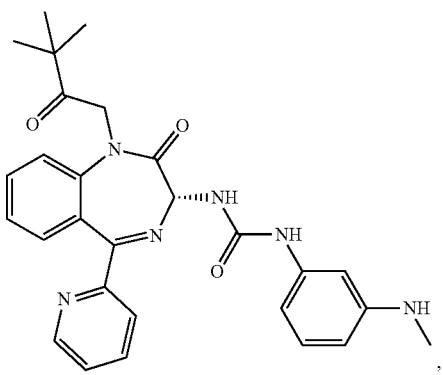

Formula (IIIb)

including any pharmaceutically acceptable, solvate or anhydrate thereof. The compound of Formula (IIb) is known as YM022 whereas the compound of Formula (IIIb) is known as YF476. These compounds may be prepared or obtained according to suitable methods.

In an alternative embodiment, the CCK2 receptor antagonist may be a molecule selected from the group consisting of: proglumide, CI-988, CI-1015, L-365260, L-369293, RP-69758, LY-255910, LY288513, PD-135158, PD-145942, and a derivative thereof.

Also contemplated by the present invention are any pharmaceutically acceptable salts, hydrates, solvates, anhydrates as well as enantiomers and their mixtures, stereoisomeric forms, racemates, diastereomers and their mixtures of the CCK2 receptor antagonist of the present invention.

The term "solvate" refers to a complex of variable stoichiometry formed by a solute, i.e. the CCK2 receptor antagonist, and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms stereoisomers, diastereomers, enantiomers and racemates are known to the skilled person.

"Treating" the epilepsy in particular includes inhibiting or partial inhibiting seizure onsets, inhibit recurrent seizures, inhibiting or reversing epileptogenesis, arresting or reversing epilepsy complications such as breathing in food or saliva into the lungs during a seizure, injury from falls, bumps, self-inflicted bites, driving or operating machinery during a seizure, permanent brain damage. In an embodiment herein, the administration of the CCK2 receptor antagonist to the subject can significantly inhibit the spontaneous recurrent seizures in the subject with a prolonged effect.

The expression "effective amount" generally denotes an amount sufficient to produce therapeutically desirable results, wherein the exact nature of the result varies depending on the specific disorder which is treated. The CCK2 receptor antagonist of the present invention may be contained in a composition, in particular a pharmaceutical composition, in an effective amount, i.e. an amount suitable to treat or prevent epilepsy in a subject, in particular a mammal.

The subject can be a human or animal, in particular the subject is a mammal, preferably a human. The subject is, thus, preferably a human suffering from epilepsy. The subject may also include human having a resistance to conventional antiepileptic drugs, i.e. the subject may have refractory epilepsy.

The effective amount of the CCK2 receptor antagonist of the present invention may depend on the species, body weight, age and individual conditions of the subject and can be determined by standard procedures such as experimental animals. In an embodiment where the subject is a mouse, the effective amount is preferably about 0.001 mg/kg, 0.01 mg/kg, 0.1 mg/kg, 1 mg/kg, 10 mg/kg, 100 mg/kg or 500 mg/kg. The effective amount of the CCK2 receptor antagonist of the present invention may be indicated by a reduction or decline of accumulative scores of spontaneous seizures of the subject for at least 3 days.

The term "epilepsy" refers to a brain disorder in which a subject has repeated seizures over time, i.e. the seizure is not a single incident and it will happen again for at least one more time. The subject suffering from epilepsy typically has a non-induced seizure for at least two times with a time interval of more than 24 hours. The term "seizure" refers to the physical findings or changes in behavior that occur after an episode of abnormal electrical activity in the brain. For the purposes of clinical assessment, it is appreciated in the art that the subject suffering from epilepsy are generally classified according to the types of seizure. The two main classes of seizures are focal onset seizures and generalized onset seizures. Focal onset seizures are further classified as aware or impaired awareness; whereas generalized seizures are further classified as motor or nonmotor (absence).

A skilled person may be aware of determining whether a subject is in needs of an anti-epilepsy or anti-seizure treatment according to the present invention based on the predisposing factors. The term "predisposing factors" generally refers to factors or conditions that render a subject vulnerable to a disease or disorder, i.e. epilepsy in present disclosure. The predisposing factors for epilepsy may include but not limited to injury or trauma of any kind to the central nervous system (CNS), infections of the CNS, cardiac arrest, brain tumor, exposure to toxic or poisonous agents, family history factors, and history of status epilepticus.

In an embodiment, the CCK2 receptor antagonist of the present invention may be administered in combination with an effective amount of one or more antiepileptic compound. The term "antiepileptic compound" includes drugs which are commonly administered to a subject having no resistance to the current antiepileptic drug therapy, i.e. which have been known to be used in the treatment of epilepsy.

In particular, the antiepileptic compound is selected from the group consisting of primidone, diazepam, perampanel, tiagabine, methsuximide, ethosuximide, stiripentol, phenobarbital sodium, felbamate, acetazolamide, brivaracetam, benzobarbital, phenytoin sodium, clobazam, fosphenytoin sodium, ezogabine, lacosamide, eslicarbazepine, topiramate, oxcarbazepine, zonisamide, lamotrigine, carbamazepine, clonazepam, vigabatrin, levetiracetam, divalproex sodium, valproic acid, lorazepam, clorazepate, and gabapentin.

The antiepileptic compound may be administered before, after or simultaneously with the CCK2 receptor antagonist, in particular before or simultaneously with the CCK2 receptor antagonist, further preferred simultaneously with the CCK2 receptor antagonist.

The CCK2 receptor antagonist according to the present invention may be administered by an oral, injective, rectal, topical, parenteral, transdermal or inhalative route to a subject. In an embodiment where the subject is a mouse, the CCK2 receptor antagonist is administered through injection to the subject. The term injection encompasses intraperitoneal, intravenous, intramuscular, subcutaneous and intradermal administration.

In another aspect, the present invention pertains to a pharmaceutical composition comprising a CCK2 receptor antagonist as described above or a pharmaceutical acceptable salt thereof as active ingredient, one or more antiepileptic compounds as described above, and a pharmaceutically acceptable excipient.

The "pharmaceutically acceptable excipient" may include pharmaceutically acceptable carriers, diluents, preserving agents, solubilizing agents, stabilizing agents, disintegrating agents, binding agents, lubricating agents, wetting agents, emulsifiers, sweeteners, colorants, odorants, salts, buffers, coating agents and antioxidants. Suitable excipients and techniques for formulating pharmaceutical composition are aware by a skilled person in the art.

Accordingly, the present invention also pertains to use of a CCK2 receptor antagonist as described above in the treatment of epilepsy, and use of the CCK2 receptor antagonist as described above in the preparation of a medicament for treatment of epilepsy.

The experiments as described below further support the antiepileptic effect of the CCK2 receptor antagonist according to the present invention.

EXAMPLES

Example 1

Adult male C57 mice were housed under standard conditions, with food and water available. For injection of kainic acid, mice were anesthetized with sodium pentobarbital (50 mg/kg, i.p.; Ceva Sante Animale Co., France), and atropine sulphate (0.05 mg/kg, s.c.) was administered to inhibit tracheal secretions. Kainic acid (0.3 mg/mL, 650 nL, Tocris), was stereotaxically injected into the right CA3 area of the hippocampus. Kainic acid was slowly injected over 60 s with a 2 μL microsyringe at the following stereotaxic coordinates: AP, −2.06; ML, −1.80; DV, −1.60, respectively. After injection, the needle of the syringe was maintained in situ for additional 5 min to limit reflux along the injection track. Directly after surgery, the mice were housed in clear plexiglass cages (one per cage). A special camera was placed diagonally above each cage for monitoring in both the light and dark phase. Exactly 2 weeks after kainic acid treatment, all videos were collected regularly, and three trained technicians blind to drug intervention viewed the videos. The seizure activities during 12-h epoch (00:00 a.m. to 12:00 p.m.) were rated with Racine scale (Electroencephalogr Clin Neurophysiol, 1972, 32(3): 281-294). Accumulative scores were recorded base on the quantity and severity of spontaneous seizures: 3=Racine scale stage-5 seizure; 2=Racine scale stage-4 seizure; 1=Racine scale stage-3 seizure; accumulative score is equal to sum of scores of seizures on daily basis.

The model of epilepsy induced in mice by kainic acid reproduces most of the clinical and neurophysiological features of human temporal lobe epilepsy. Unilateral intra-hippocampal injection of kainic acid induced a limbic status epilepticus which may last for up to 5 hours. This acute period is followed by a "silent" seizure-free phase lasting for a mean duration of 2 weeks after which all mice exhibit spontaneous recurrent seizures through their live.

After a period of constant spontaneous seizure onset, 5 mice intraperitoneally injected YM022 (100 nM, 10 μL), and 9 mice intraperitoneally injected YF476 (1 μM, 10 μL).

Figure 2:
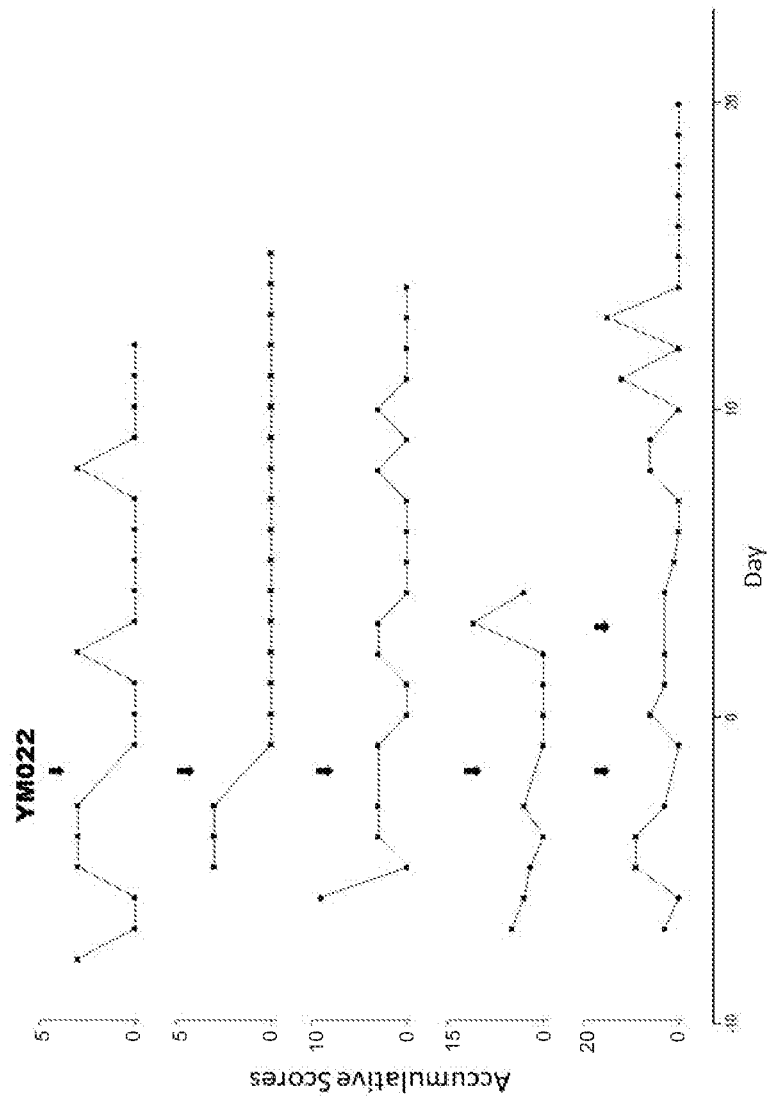
FIG. 2 is a series of line plots depicting the statistics of the accumulative scores of spontaneous seizures of epilepsy model mice before and after single or multiple drug interventions (YM022, 100 nM, 10 µL). The 5 lines represent 5 epilepsy model mice of the experiment, and the black arrows indicate the time of drug interventions.

As shown in FIGS. 1 and 2, the epilepsy mouse models were assigned to an accumulative score of at least 3 on the day before the drug interventions. That is, the epilepsy mouse models exhibited at least a Racine scale stage-5 seizure. After treating the mice either with YM022 or YF476, there was a significant reduction of the accumulative scores for at least 3 days, and the seizure onsets became very rare after multiple injections, possibly suggesting the prolonged half-life of the CCK2 antagonists.

The invention claimed is:

1. A method of treating a subject suffering from epilepsy comprising: administering an effective amount of a cholecystokinin-2 receptor antagonist having a structure of Formula (Ia) or a pharmaceutical acceptable salt thereof to the subject,

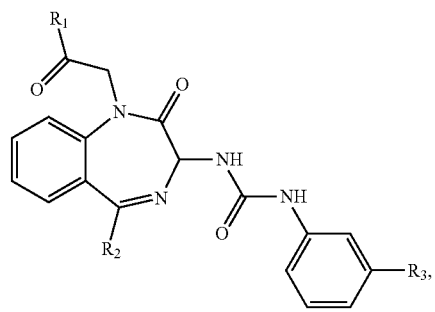

Formula (Ia)

wherein $R_1$ and $R_2$ are independently a hydrogen atom, a substituted or unsubstituted linear or branched chain C1 to C5 alkyl group, a substituted or unsubstituted aryl group, or a heteroaryl; and $R_3$ is a hydrogen atom, a substituted or unsubstituted linear or branched chain C1 to C3 alkyl group, or a C1 to C3 alkylamino group.

2. The method of claim 1, wherein the cholecystokinin-2 receptor antagonist has a structure of Formula (Ia) with $R_1$ being a linear or branched chain C1 to C4 alkyl group, or a substituted or unsubstituted aryl group; $R_2$ being a substituted or unsubstituted aryl group, or a heteroaryl; and $R_3$ being a methyl group, an ethyl group, a methylamino group or an ethylamino group.

3. The method of claim 1, wherein the cholecystokinin-2 receptor antagonist has a structure of Formula (IIa) or Formula (IIIa):

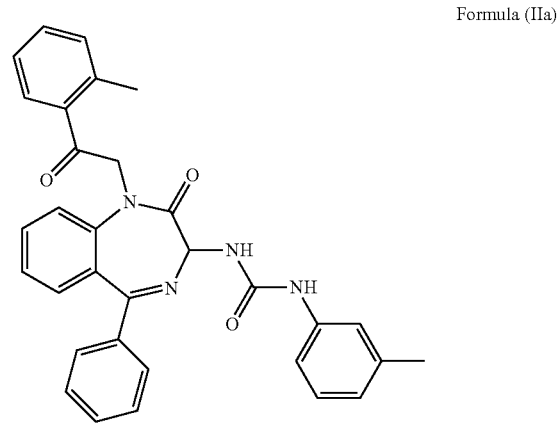

Formula (IIa)

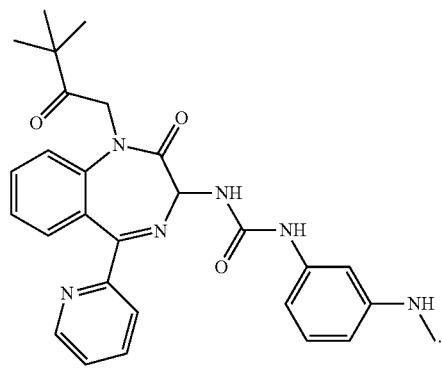

Formula (IIIa)

4. The method of claim 1, wherein the cholecystokinin-2 receptor antagonist has a structure of Formula (IIb) or Formula (IIIb):

Formula (IIb)

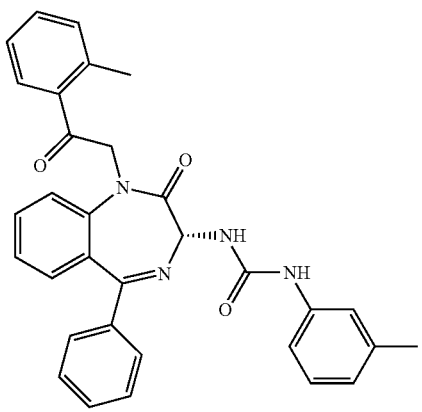

Formula (IIIb)

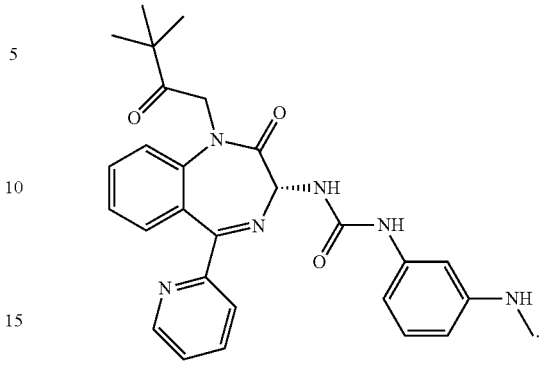

5. The method of claim 1, wherein the cholecystokinin-2 receptor antagonist is administered in combination with one or more antiepileptic compounds to the subject.

6. The method of claim 5, wherein the antiepileptic compound is selected from the group consisting of primidone, diazepam, perampanel, tiagabine, methsuximide, ethosuximide, stiripentol, phenobarbital sodium, felbamate, acetazolamide, brivaracetam, benzobarbital, phenytoin sodium, clobazam, fosphenytoin sodium, ezogabine, lacosamide, eslicarbazepine, topiramate, oxcarbazepine, zonisamide, lamotrigine, carbamazepine, clonazepam, vigabatrin, levetiracetam, divalproex sodium, valproic acid, lorazepam, clorazepate, and gabapentin.

7. The method of claim 1, wherein the cholecystokinin-2 receptor antagonist is administered to the subject via injection.

* * * * *